(12) United States Patent
Griggs

(10) Patent No.: US 6,447,513 B1
(45) Date of Patent: Sep. 10, 2002

(54) FIXATION DEVICE

(76) Inventor: Ian Ross Griggs, Wookey Barn, Lot 5, Homestead Road, Wonga Park, Victoria 3115 (AU)

( * ) Notice: Subject to any disclaimer, the term of this patent is extended or adjusted under 35 U.S.C. 154(b) by 0 days.

(21) Appl. No.: 09/830,768
(22) PCT Filed: Oct. 28, 1999
(86) PCT No.: PCT/AU99/00937
§ 371 (c)(1), (2), (4) Date: Jul. 2, 2001
(87) PCT Pub. No.: WO00/25690
PCT Pub. Date: May 11, 2000

(30) Foreign Application Priority Data

| Oct. 30, 1998 | (AU) | PP 6847 |
| May 13, 1999 | (AU) | PQ 0336 |

(51) Int. Cl.⁷ .............................................. A61B 17/68
(52) U.S. Cl. ..................................................... 606/62
(58) Field of Search ........................ 606/60, 62, 63, 606/64, 67, 68, 66, 72

(56) References Cited

U.S. PATENT DOCUMENTS

| 4,237,875 A | | 12/1980 | Termanini | |
| 4,327,753 A | * | 5/1982 | Bertschi | 132/40 |
| 4,335,732 A | * | 6/1982 | Megna | 132/123 |
| 4,411,281 A | | 10/1983 | Doern | |
| 4,473,086 A | * | 9/1984 | Thaler et al. | 132/37 R |
| 5,057,103 A | * | 10/1991 | Davis | 606/63 |
| 5,759,184 A | * | 6/1998 | Santangelo | 606/68 |
| 5,810,820 A | * | 9/1998 | Santori et al. | 606/63 |
| 5,971,986 A | * | 10/1999 | Santori et al. | 606/62 |

FOREIGN PATENT DOCUMENTS

| AU | 2853584 | 11/1984 | |
| WO | WO9639584 | 12/1996 | |
| WO | WO-9737606 A | * 10/1997 | 606/62 |
| WO | WO9748352 | 12/1997 | |
| WO | WO9851228 | 11/1998 | |

* cited by examiner

Primary Examiner—Eduardo C. Robert
(74) Attorney, Agent, or Firm—Richard M. Goldberg (57) ABSTRACT

A fixation device comprises an outer hollow elongate member having a plurality of holes in its outer wall, and an inner member carrying a plurality of pins, such that the device is placed in a suitable cavity and the pins are extended through the respective holes.

36 Claims, 4 Drawing Sheets

FIXATION DEVICE

BACKGROUND OF THE INVENTION

The present invention relates to an intramedullary bone fixation device and to a method of fixing an intramedullary device to a bone. The apparatus and method of the present invention are especially suitable for stabilising bone fractures and for fixing prostheses, such as artificial hips, knees or other joints, into bones.

The present invention also relates to an apparatus for fixing to a structure, beam, member, wall, or the like. The apparatus may be adapted to have other connecting apparatus, such as bolts, screws, nails, hooks or the like affixed thereto, or it may be adapted to join elements, such as bricks, beams, or the like, together.

Fixation and stabilisation of fractures can be difficult, especially in long bones. Two techniques are normally used. The first technique involves placing a plate on one side of the bone and screwing the plate to the bone on either side of the fracture with a plurality of screws. This technique suffers from the disadvantage that forces are applied to the bone via the screws from one side of the bone only, which can cause uneven loading on the bone.

The second technique for fixation and stabilisation of fractures involves inserting an intramedullary pin into the medullary canal of the bone. Fixation pins may or may not be used. If fixation pins are not used, the bone at either side of the fracture may rotate around the intramedullary pin which leads to misalignment of the bone. If fixation pins are used, it is necessary to drill holes through the bone on either side of the fracture and insert fixation pins through the holes in the bone and through holes formed in the intramedullary pin. It is often difficult to align the holes in the bone with those in the intramedullary pin, thereby complicating the operative procedure and potentially causing an increase in post-operative recovery time for the patient.

Fixation of prosthesis, such as artificial hips and artificial knees, also faces similar difficulties. For example, fitting an artificial hip to a patient typically involves preparing the upper part of the femur and inserting a stem portion of the hip prosthesis into the medullary canal of the femur. The stem is fixed to the femur by bone cement or by inserting external pins through holes drilled through the femur and into and through holes in the stem portion of the artificial hip. The difficulties with using external pins have been discussed above. In cases where bone cement is used, misalignment and shifting of the prostheses can occur if the cement does not adequately adhere to the bone.

It is an object of the present invention to provide a device and a method that overcomes or at least ameliorates one or more of the above-mentioned disadvantages of the prior art.

In a first aspect, the present invention provides an intramedullary bone fixation device comprising a hollow elongate member having at least one opening in a side wall thereof, the hollow elongate member being adapted for insertion into a medullary canal of a bone, and an inner member sized to be slidably receivable within the hollow elongate member, the inner member carrying at least one pin, the inner member having one or more grooves in an outer surface thereof, said at least one pin being positioned in the one or more grooves when the at least one pin is in a retracted position, at least one pin being pivotally connected at one end thereof to the inner member, the at least one pin being movable from a retracted position to an extended position in which the at least one pin extends through respective ones of the at least one opening in the hollow elongate member, and wherein the at least one pin as moved to the extended position by placing free ends of the at least one pin into alignment with the one or more openings and rotating the inner member to thereby extend the pins through the one or more openings.

In another aspect, the present invention provides an intramedullary bone fixation device comprising a hollow elongate member having at least one opening in a side wall thereof, the hollow elongate member being adapted for insertion into a medullary canal of a bone, and an inner member sized to be slidably receivable within the hollow elongate member, the inner member carrying at least one pin, the at least one pin being movable from a retracted position to an extended position in which the at least one pin extends through respective ones of the at least one opening in the hollow elongate member, wherein the at least one pin has an enlargement at one end thereof and the enlargement rests in a respective hole or recess formed in the inner member and the at least one pin extends along respective grooves formed in the inner member when in the retracted position, wherein the one or more pins are retained in place by an inner wall of the hollow elongate member and the one or more pins are extended by aligning free ends thereof with the at least one opening in the hollow elongate member and rotating the inner member.

The distal end of the hollow elongate member may have a point or a closed end at the distal end thereof to facilitate insertion of the hollow elongate member into the medullary canal. The distal end of the hollow elongate member is preferably provided with a conical point, which may be formed integrally with the hollow elongate member or provided as a separate part that is subsequently affixed to the hollow elongate member.

The inner member is preferably a solid member but it may also comprise a hollow member. The inner member is preferably sized to fit snugly but not too tightly into the hollow elongate member to thereby allow easy movement of the inner member within the hollow elongate member whilst avoiding slack or "looseness" between the inner member and the hollow elongate member. Preferably, both the inner member and the hollow elongate member are cylindrical for a major portion of their length.

The inner member carried the at least one pin. It is preferred that the inner member carries a plurality of pins. The hollow elongate member should have at least the same number of openings in its side wall as pins on the inner member. Alternatively, the opening(s) may be shaped such that two or more pins may extend therethrough. For example, the hollow elongate member may be provided with a slot through which two or more pins may project The one or more pins are the means by which the device of the present invention is held in position with respect to the bone. In use of the device of the present invention, the device is inserted into the intramedullary canal of the bone. Once in the desired position, the pins are moved from the retracted position to the extended position. In the extended position, the or each pin extends through a hole in the side wall of the hollow elongate member and into the bone, thereby fixing the relative position of the device and the bone. The device is simple to use because it does not require holes to be drilled through the bone to cater for external fixing pins. It also securely holds the bone in position relative to the device.

In preferred embodiments of the present invention, a plurality of pins are carried by the inner member in order to firmly fix or connect the device to the bone. For convenience of description, the invention will hereinafter be described with reference to a plurality of pins. However, it will be understood that the objects of the present invention could be met with a single pin and that such an embodiment falls within the scope of the present invention.

In the retracted position, the pins preferably do not extend beyond the outer diameter or perimeter of the hollow elongate member. In the extended position, the pins extend through the holes in the side wall of the hollow elongate member and into the bone.

In the preferred embodiment of the present invention, the inner member is provided with one or more grooves in an outer surface thereof. Such grooves are suitably generally transverse grooves. The pins are placed in the grooves and pivotally connected at or near one end to the inner member. The other end of each pin may extend slightly beyond the surface of the inner member. In order to move the pins to the extended position, the inner member may be rotated or turned when the free ends of the pins are in alignment with the holes in the side wall of the hollow elongate member. The free ends of the pins will extend through the holes. As rotation of the inner member continues, the distance between the pivotally mounted ends of the pins and the holes in the hollow elongate member decreases and this causes the pins to move outwardly through the holes until they are fully extended.

In order to enable the inner member to be rotated with the force required to extend the pins into the bone, the proximal end of the inner member may be provided with an engaging surface for engaging with a handle or a torque applying means. To avoid or minimise rotation of the hollow elongate member may also be provided with a holding surface for holding the hollow elongate member in position. The holding surface may be a square, rectangular, hexagonal or other polygonal surface on the proximal end of the hollow elongate member. Alternatively, the hollow elongate member may be provided with a keyway to engage with a suitable tool to hold the hollow elongate member in position.

The hollow elongate member and the inner member may be fixed length members or they may be of variable or adjustable length. Variable or adjustable length members are especially useful in cases where the device is used for fixating fractures and it is desirable to adjust the length of the device during healing of the fracture.

The present invention also encompasses a method of fixing an intramedullary device to a bone comprising providing an intramedullary bone fixation device comprising a hollow elongate member having at least one opening in a side wall thereof, the hollow elongate member being adapted for insertion into a medullary canal of a bone, and an inner member sized to be slidably receivable within the hollow elongate member, the inner member carrying at least one pin, the at least one pin being movable from a retracted position toan extended position in which the at least one pin extends through respective one or ones of the at least one opening in the hollow elongate member, inserting the intramedullary device into the medullary canal of the bone, and extending the at least one pin from the retracted position to the extended position in which the pins extend through respective one or ones of the at least one opening in the side wall of the hollow elongate member and into the bone to thereby fix the relative position of the device and the bone.

Preferably, the device is provided with a plurality of pins.

In one embodiment, the step of inserting the device into the medullary canal of the bone comprises inserting the hollow elongate member into the medullary canal and subsequently inserting the inner member into the hollow elongate member. Alternatively, this step may comprise inserting the inner member into the hollow elongate member and subsequently inserting the hollow elongate member into the medullary canal. As a further alternative, this step may comprise partly inserting the inner member into the hollow elongate member, inserting the hollow elongate member into the medullary canal and then fully inserting the inner member into the hollow elongate member.

The step of moving the pins from the retracted position to the extended position may comprise rotating the inner member to thereby move the pins so that they extend through the at least one hole in the side wall of the hollow elongate member. The hollow elongate member is preferably held in position whilst the inner member is rotated.

Preferably, pins extend into the bone on either side of a fracture once the device has been fitted, if the device is being used for stabilising or fixing a fracture.

The present invention also provides an apparatus that can be used in the building industry or other industries as a connector or connections or for joining two or more elements together or for fixing to a structure, beam, member, wall or the like.

In another aspect, the present invention provides an apparatus for fixing to a structure, beam, member or the like comprising a hollow elongate member having at least one opening in a side wall thereof, the hollow elongate member being adapted for insertion into a hole in a structure, beam, member or the like, and an inner member that is insertable into the hollow elongate member, the inner member carrying at least one pin, the inner member having one or more grooves in an outer surface thereof, said at least one pin being positioned in the one or more grooves when the at least one pin is in a retracted position, the at least one pin being pivotally connected at one end thereof to the inner member, the at least one pin being movable from a retracted position to an extended position in which the at least one pin extends through respective ones of the at least one opening in the hollow elongate member, and wherein the at least one pin as moved to the extended position by placing free ends of the at least one pin into alignment with the one or more openings and rotating the inner member to thereby extend the pins through the one or more openings.

In yet a further aspect, the present invention provides an apparatus for fixing to a structure, beam, member or the like comprising a hollow elongate member having at least one opening in a side wall thereof, the hollow elongate member being adapted for insertion into a hole in the structure, beam, member or the like, and an inner member in the hollow elongate member, the inner member carrying at least one pin, the at least one pin being movable from a retracted position to an extended position in which the at least one pin extends through respective ones of the at least one opening in the hollow elongate member, wherein the at least one pin has an enlargement at one end thereof and the enlargement rests in a respective hole or recess formed in the inner member and the at least one pin extends along respective grooves formed in the inner member when in the retracted position, wherein the one or more pins are retained in placed by an inner wall of the hollow elongate member and the one or more pins are extended by aligning free ends thereof with the at least one opening in the hollow elongate member and rotating the inner member.

The distal end of the hollow elongate member, being the end that is inserted into the hole in the structure, member, beam, wall or the like, preferably has a closed end. This will avoid the hollow elongate member possibly filling with debris when inserted into the hole in the structure or the like (hereinafter, the term "structure or the like" will be used to refer to the "structure, beam, member, wall or the like" for the sake of brevity). A closed end on the hollow elongate member will also act as a stop member for the inner member and ensure that the inner member is inserted to the to the correct depth into the hollow elongate member. The distal end of the hollow elongate member may be provided with a pointed or generally conical end to assist with insertion into the hole of the structure or the like.

The inner member is preferably a solid member but it may also comprise a hollow member. The inner member is preferably sized to fit snugly but not too tightly into the hollow elongate member whilst avoiding slack or "looseness" between the inner member and the hollow elongate member. Preferably, both the inner member and the hollow elongate member are cylindrical for a major portion of their length.

The inner member carried the at least one pin. It is preferred that the inner member carries a plurality of pins. The hollow elongate member should have at least the same number of openings in its side wall as pins on the inner member. Alternatively, the opening(s) may be shaped such that two or more pins may extend therethrough. For example, the hollow elongate member may be provided with a slot through which two or more pins may project.

The one or more pins are the means by which the device of the present invention is connected to the structure or the like. In use, the apparatus is inserted into a hole in the structure or the like. The hole in the structure or the like may be made by drilling or by forming during manufacture or construction of the structure or the like. When the apparatus has been inserted to the desired depth, the pins are moved from the retracted position to the extended position in which the pins extend into the material of the structure or the like to thereby fix or connect the apparatus to the structure or the like.

In order to ensure that the apparatus is inserted to the correct depth in the hole in the structure or the like, some embodiments of the present invention may include a flange or outwardly extending abutment member on the proximal end of the hollow elongate member to ensure that the proximal end of the hollow elongate member lies flush with the outer surface of the structure of the like.

In a preferred embodiment of this aspect of the present invention, the inner member is provided with one or more grooves in an outer surface thereof. Such grooves are suitably generally transverse grooves. The pins are placed in the grooves and pivotally connected at or near one end to the inner member. The other end of each pin may extend slightly beyond the surface of the inner member. In order to move the pins to the extended position, the inner member may be rotated or turned when the free ends of the pins are in alignment with the holes in the side wall of the hollow elongate member. The free ends of the pins will extend through the holes. As rotation of the inner member continues, the distance between the pivotally mounted ends of the pins and the holes in the hollow elongate member decreases and this causes the pins to move outwardly through the holes until they are fully extended.

In order to enable the inner member to be rotated with the force required to extend the pins into the material of the structure or the like, the proximal end of the inner member may be provided with an engaging surface for engaging with a handle or torque applying means. The torque applying means may be a spanner, wrench, screwdriver, pliers or the like.

The apparatus of the present invention may be fixed or connected to the structure or the like to enable other devices to be fixed thereto. For example, the inner member may be provided with an internal thread to enable another screw or bolt to be joined thereto.

Alternatively, the inner member may extend out of the hollow elongate member (and extend outwardly from the outer wall or surface of the structure or the like when the apparatus is fixed or connected) and the outwardly extending part of the inner member could be used to join or connect other elements thereto.

The apparatus of the present invention could also be used as a fixation device for connecting two structures or the like, such as planks, beams, or bricks together. In this case, holes would have to be made in both of the articles to be connected.

BRIEF DESCRIPTION OF THE DRAWINGS

The present invention will now be described further with reference to the accompanying drawings, which show a preferred embodiment of the invention. It will be appreciated that the accompanying drawings are provided to illustrate the invention and the present invention should not be considered to be limited to the particular embodiment shown in the drawings. In the drawings.

Figures 1, 2, 4:
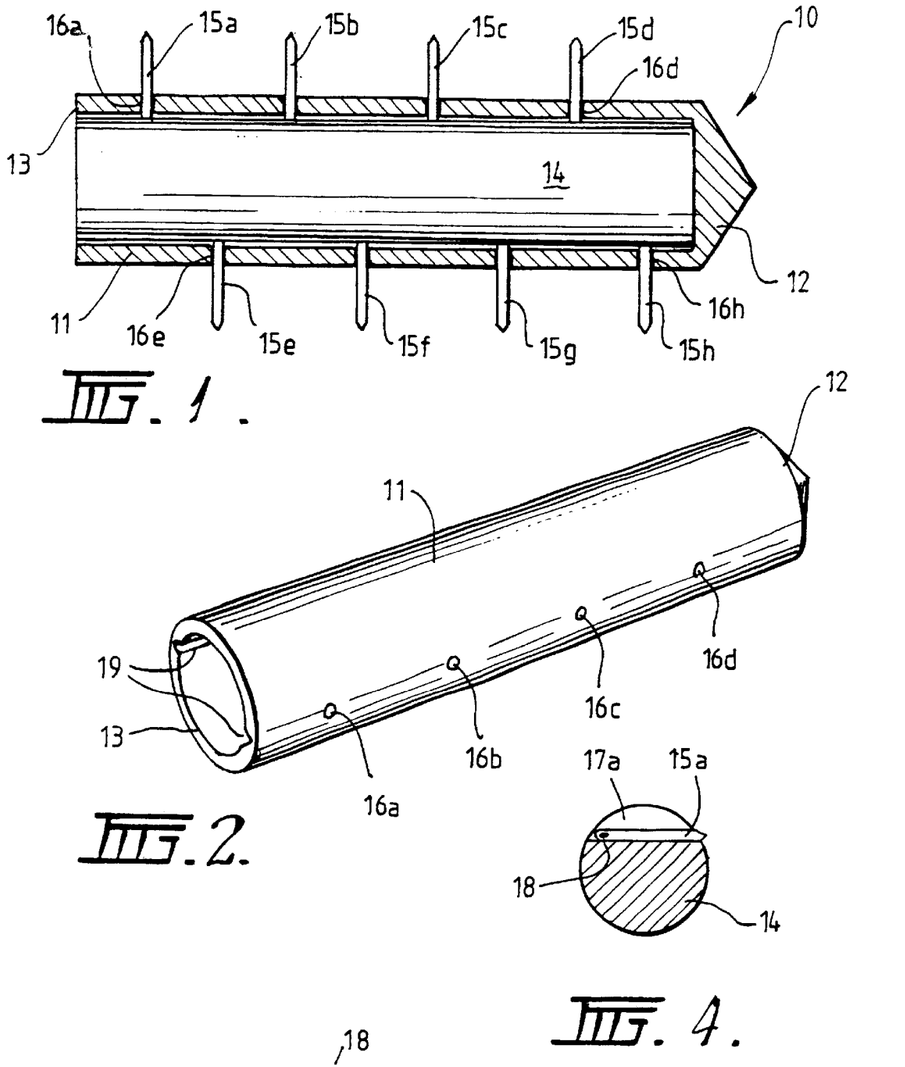
FIG. 1 shows a cross-sectional side view of a device in accordance with the present invention with the pins in the extended position.
FIG. 2 shows a perspective view of the hollow elongate member of the device of FIG. 1.
FIG. 4 is a cross-sectional end view taken along line 4—4 of FIG. 3.

FIG. 1 shows an apparatus 10 in accordance with the present invention. The apparatus 10 includes a hollow elongate member 11 which has a distal end 12 that has a closed conical point formed thereon and an open proximal end 13. An inner member 14 having a plurality of pins 15a, 15b, ... 15h mounted thereon. The pins 15a to 15h extend through respective holes 16a to 16h. Holes 16a to 16d are more clearly shown in FIG. 2.

Figure 3:
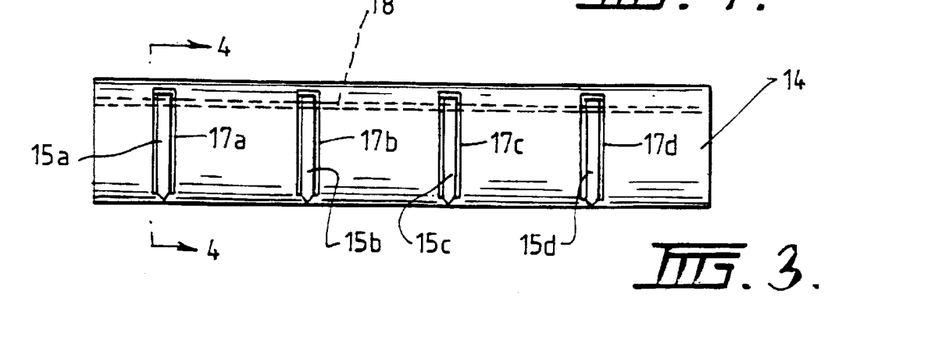
FIG. 3 is a top view of the inner member of FIG. 1 with the pins in the retracted position.

Turning now to FIGS. 3 and 4, which show some details of the inner member 14 of the device of the present invention, the inner member 14 comprises a solid pin having a plurality of transversely extending grooves 17a, 17b, 17c, 17d formed therein, for example, by machining. The grooves 17a to 17d house respective pins 15a to 15d when the pins are in the retracted position. A wire or nail 18 extends along a substantial part of the length of inner member 14 and through one end of each of the pins 15a to 15d to thereby pivotally mount the pins 15a to 15d to the inner member 14.

As is best shown in FIG. 4, the free end of pin 15a extends beyond the outer surface of inner member 14. In order to ensure that the inner member 14 can be inserted into the hollow elongate member 11 without the free end of the pins catching on the inner surface of the hollow elongate member 11, the hollow elongate member 11 may be provided with one or more longitudinally extending grooves 19 (see FIG. 2) in which the tips of the free ends of the pins can extend. It will be appreciated that the longitudinally extending groove 19 extends along the same line as the row of holes 16a to 16d.

Figures 5, 6, 7, 8, 9:
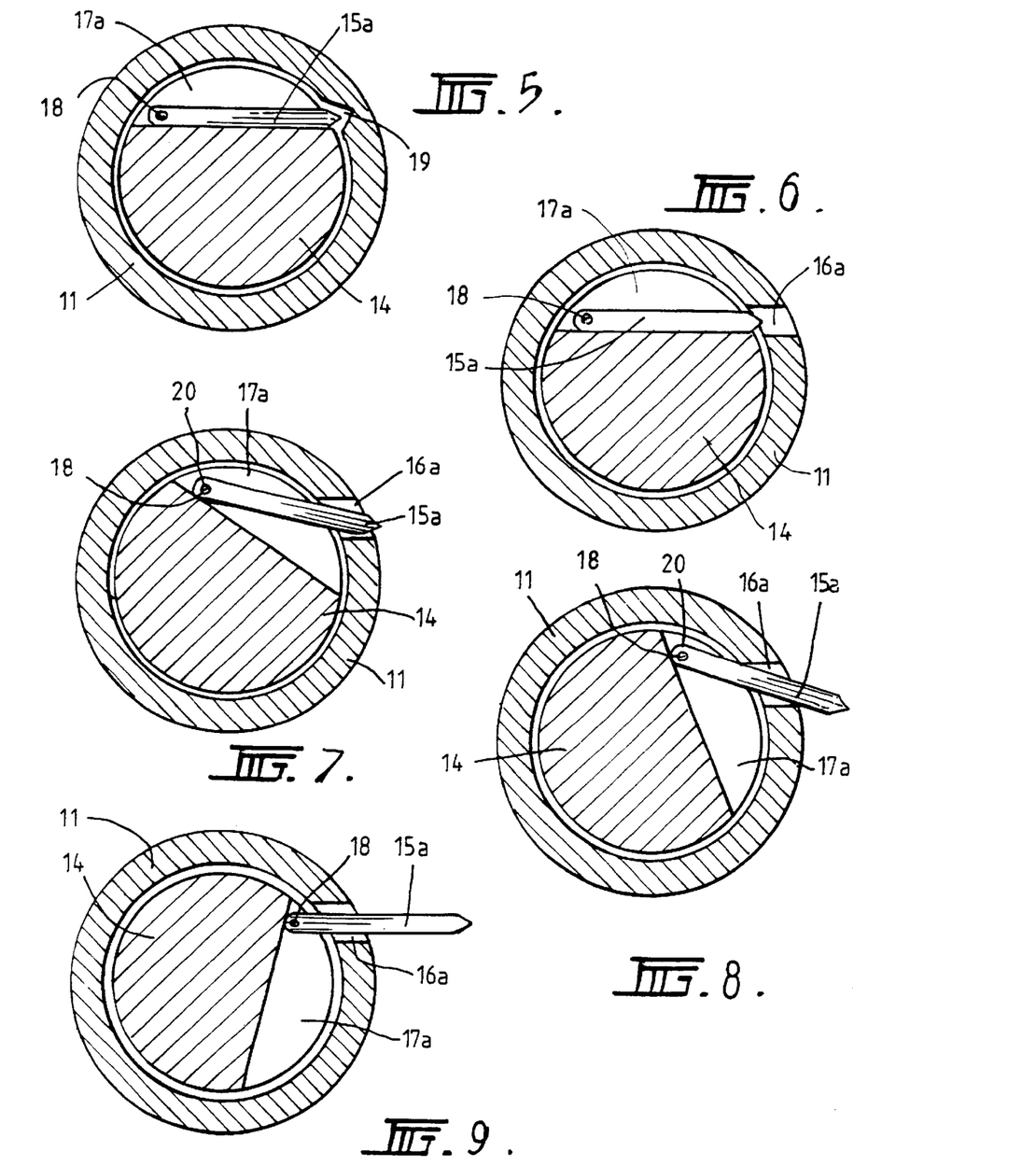
FIG. 5 is an end cross-sectional view showing the inner member inserted into the hollow elongate member.
FIGS. 6 to 9 are end cross-sectional views showing the pin moving from the retracted position to the extended position.

The positioning of the fixing pin 15a relative to the groove 19 is more clearly shown in FIG. 5.

FIGS. 6 to 9 show the manner in which the fixing pin 15a is moved from the retracted position (shown in FIG. 6) to the extended position (shown in FIG. 9). In particular, the inner member 14 is slid along the central bore of hollow elongate member 11, with the tip of pin 15a moving in groove 19, until the fixing pin 15a comes into alignment with hole 16a (as shown in FIG. 6). As can be seen from FIG. 6, the tip of fixing pin 15a extends a short distance into hole 16a, but in the retracted position the tip of fixing pin 15a does not extend beyond the outer periphery of hollow elongate member 11.

In order to move the fixing pin 15a from its retracted position, the inner member 14 is rotated, typically by applying a turning force to its proximal end. As inner member 14 is rotated, the tip of fixing pin 15a is caught by the edges of the hole 16a. As rotation of the inner member 14 continues, the point 20 at which the fixing pin 15a is pivotally mounted to the wire 18 moves closer to the hole 16a. This acts to force the pin 15a to extend outwardly through the hole 16a. Further rotation, as shown in FIGS. 8 and 9, forces the pin to extend even further until it is in the fully extended position as shown in FIG. 9.

Figures 10, 11, 12, 14, 15:
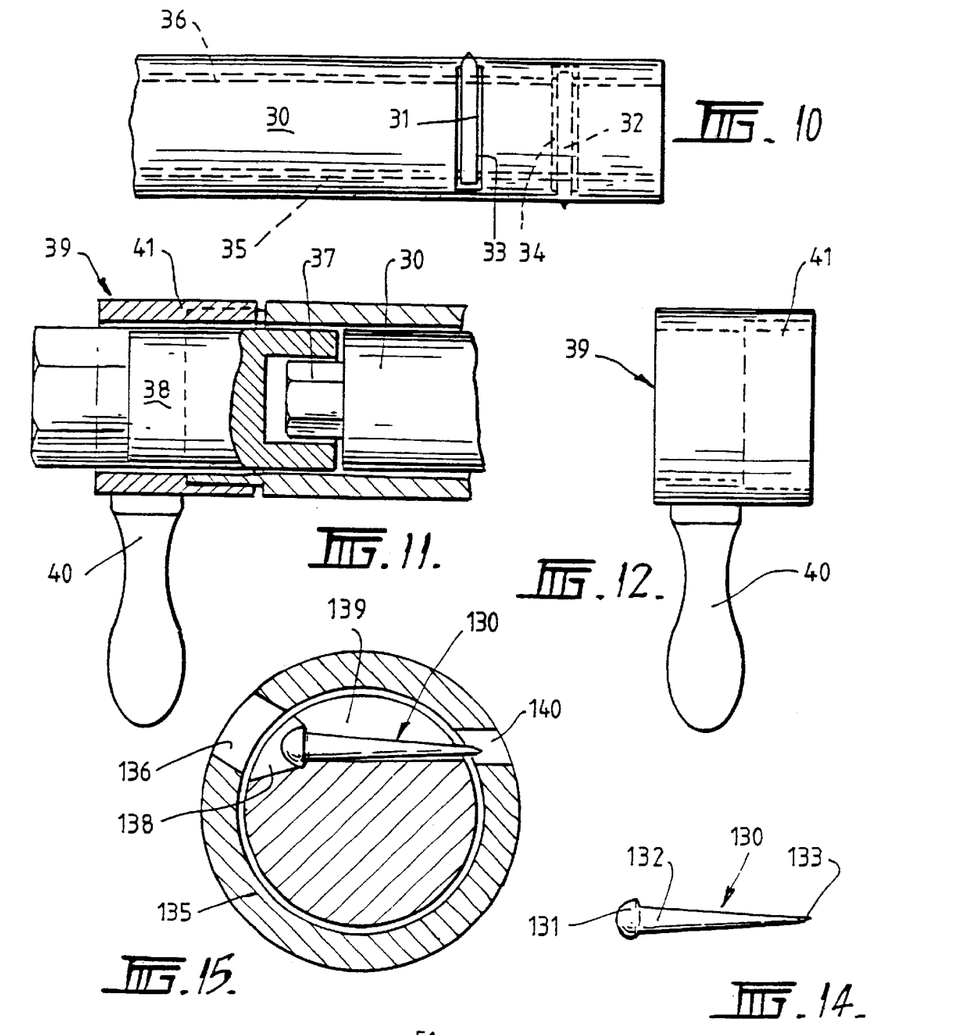
FIG. 10 is a cross-sectional side view of another embodiment of the present invention.
FIG. 11 is a side view, partly in cross section, of the proximal end of an apparatus in accordance with the present invention.
FIG. 12 is a schematic diagram of the hollow elongate member holding means shown in FIG. 11.
FIG. 14 is a side view of a pin or nail suitable for use in another embodiment of the present invention.
FIG. 15 is a cross-sectional end view of another embodiment of the present invention.

FIG. 10 shows a schematic diagram of an inner member 30 that has fixing pins 31, 32 mounted in diametrically opposed positions. The pins 31, 32 are fitted in grooves 33, 34 and are held by respective nails 35, 36 that pivotally connect the pins 31, 32 to the inner member 30.

In order to facilitate fixing the device of the present invention into the medullary canal, it is preferred that both the inner member and the hollow elongate member are fitted or shaped at their proximal end with features that enable tools or holding means to be applied thereto. This is best shown in FIG. 11 in which the inner member 30 has a square or hexagonal projection 37 formed on its proximal end to engage with the complementarily shaped tool 38 having a handle (not shown) that can apply a torque or turning force thereto. It is especially preferred that the tool 38 has a ratchet handle fitted to enable easier application of the turning force.

In order to prevent the hollow elongate member turning when the rotational force is applied to the inner member to extend the pins, it is preferred that the outer hollow elongate member has holding means formed on the proximal end thereof, which holding means may include a square, rectangular, hexagonal or other polygonal shaped ending that can engage with a stabilising tool 39. As more clearly shown in FIG. 12, the stabilising tool 39 includes a handle 40 and an engaging portion 41 that engages with the proximal end of the hollow elongate member.

Figure 13:
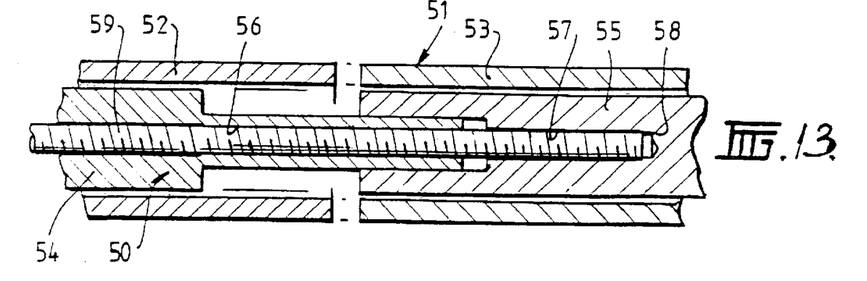
FIG. 13 is a schematic, cross-sectional view of a further embodiment of the present invention of variable length.

FIG. 13 shows another embodiment of the present invention in which the intramedullary bone fixation device is of expandable length. In particular, the device shown in FIG. 13 includes an inner member 50 and an outer member 51 that includes a first portion 52 and a second portion 53. Inner member 50 also includes a first portion 54 and a second portion 55. First portion 54 includes a bore 56 having at least a small threaded portion thereon. A bore 57 is also included in the second portion 55 of inner member 50 and bore 57 terminates in a blind end 58. A screw 59 is threadably inserted into bores 56, 57. When the screw has been fully inserted, the end of the screw strikes the blind end. Further rotation of the screw then acts to expand the length of the inner member 50 by pushing apart the two portions 54, 55. As the pins have been inserted into the bone surrounding the medullary canal, as the inner member 50 is expanded in length, the outer member 51 also expands in length.

It is also preferred that the proximal end of the inner member is provided with some marking in order to enable the alignment of the inner member to be readily ascertained.

Turning now to FIGS. 14 and 15, which show another embodiment of the present invention, a pin or nail 130 has a spherical portion 131 at one end with the shank 132 of the nail extending from the spherical portion 131 and tapering to a point 133. The pin or nail 130 shown in FIG. 14 is one of a plurality of such pins or nails used in the apparatus of the present invention.

The hollow elongate member 135 (see FIG. 15) has at least one hole 136 formed therein, with the at least one hole 136 having a diameter slightly larger than the diameter of the spherical portion 131 of pin or nail 130. The inner member includes a similar sized hole 138 and a groove 139 runs through this hole transverse to the length of the inner member. In order to load the pin or nail 130 with the apparatus, holes 136 and 138 are aligned and the pin or nail is inserted through the holes until the spherical portion 131 of pin or nail 130 rests in hole 138. The point 133 of pin or nail 130 extends into a slot or hole 140 almost opposite hole 136.

When the pin or nail 130 is loaded the outer tube is turned clockwise until the hole 138 in the inner member is covered by the outer tube. The slot 140 moves at the same time and just contacts the distal end of the point 132 of the pin or nail 130. The pin or nail 130 is now armed and ready for insertion.

Once the apparatus has been inserted into an appropriately sized hole in the structure or the like, the inner member is rotated in a clockwise direction until the pins or nails 130 are fully extended. In this regard, extension of the pins or nails is similar to that as shown in FIGS. 6 to 9.

In the embodiment shown in FIGS. 14 and 15, the pins or nails 130 are not connected to or mounted to the inner member. Rather, they are retained in place by the interaction between the outer tube (or hollow elongate member) and the inner member. In this sense, it will be appreciated that the inner member is still carrying the at least one pin or nail even though there is no physical mounting between the inner member and the at least one pin or nail.

Figure 16:
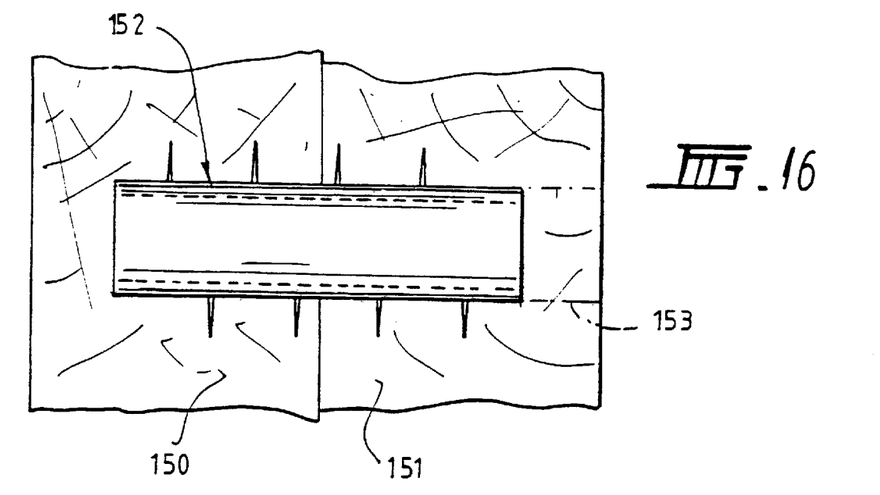
FIG. 16 is a side view, partly in cross-section, showing the apparatus in accordance with the present invention being used to hold the beams together.
Figure 17:
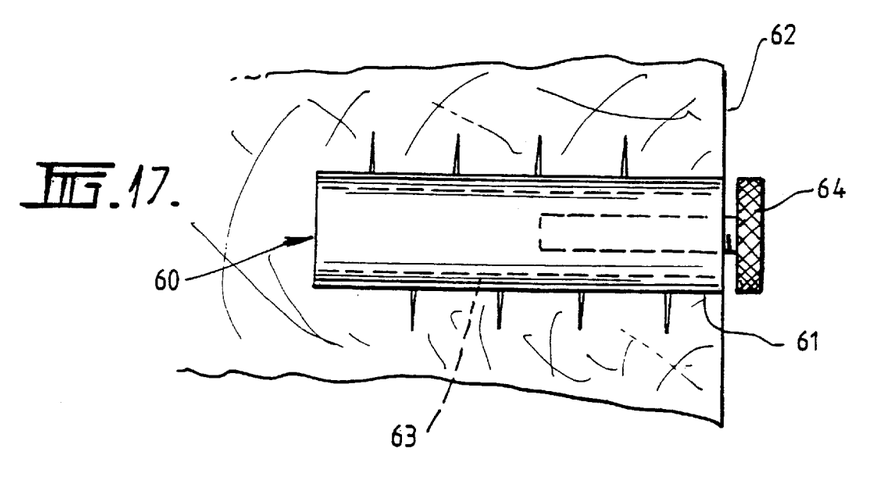
FIGS. 17 and 18 show embodiments of the present invention in which the apparatus is fixed to a wall.
Figure 18:
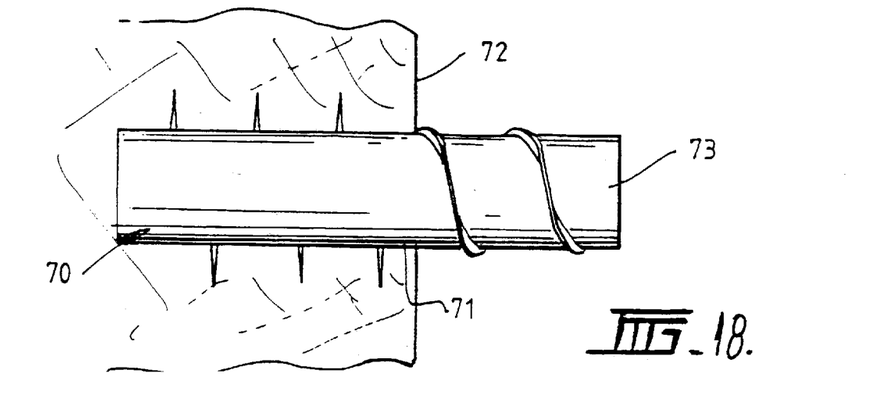

Some uses of the embodiments of the present invention in the building industry are shown in FIGS. 16, 17 and 18. In FIG. 16, two beams 150, 151 are joined together by apparatus 152 of the present invention. Apparatus 152 is inserted through hole 153 drilled in beam 151 and into an aligned hole drilled in beam 150. The inner member is then rotated, for example by use of a socket, and the pins or nails moved to the extended position as shown in FIG. 16.

In FIG. 17, the apparatus 60 of the present invention is inserted into a hole 61 drilled into the surface of a wall 62. The inner member 63 is rotated to fully extend the nails or pins and hold the apparatus in position in the wall 62. The inner member 63 has an internal thread formed therein and screw or bolt 64 can be screwed into the internal thread.

In FIG. 18, the apparatus 70 of the present invention is inserted into a hole 71 formed in wall 72 and the pins or nails extended to hold the apparatus in position. The inner member has a proximal end 73 that extends out beyond the surface of wall 72 and this can be used to bolt things onto.

Although not shown, in the embodiments of FIGS. 17 and 18 the hollow elongate member or outer tube may be provided with an outwardly extending flange, lip or projection on the proximal end thereof to ensure that the proximal end lies substantially flush with the outer surface of the wall.

It will be appreciated that the embodiment of the present invention shown in FIGS. 14 and 15 may also be used in the intramedullary bone fixation device described in the first aspect of the present invention.

Those skilled in the art will appreciate that the invention described herein is susceptible to variations and modifications other than those specifically described. It will be understood that the present invention encompasses all such variations and modifications that fall within its spirit and scope.

What is claimed is:

1. An intramedullary bone fixation device comprising:
   a hollow elongate member having at least one opening in a side wall thereof, the hollow elongate member being adapted for insertion into a medullary canal of a bone, and
   an inner member sized to be slidably receivable within the hollow elongate member, the inner member carrying at least one pin, the inner member having at least one groove in an outer surface thereof, said at least one groove extending in a direction that is generally transverse to a longitudinal axis of the inner member, said at least one pin being positioned in the at least one groove when the at least one pin is in a retracted position, at least one said pin being pivotally connected at one end thereof to the inner member, the at least one pin being movable from a retracted position to an extended position in which the at least one pin extends through respective ones of the at least one opening in the hollow elongate member, and wherein the at least one pin is moved to the extended position by placing free ends of the at least one pin into alignment with the at least one opening and rotating the inner member to thereby extend the at least one pin through the at least one opening.

2. A device as claimed in claim 1 wherein a free end of the at least one pin extends slightly beyond the outer surface of the inner member.

3. A device as claimed in claim 2 wherein the free ends of the at least one pin extend into respective ones of the at least one opening when in the retracted position.

4. A device as claimed in claim 2 wherein an inner wall of the hollow elongate member is provided with a groove for receiving the free ends of the at least one pin to thereby allow longitudinal insertion of the inner member into the hollow elongate member.

5. A device as claimed in claim 1 wherein the at least one pin is pivotally mounted at one end such that rotation of the inner member causes the pivotally mounted end of the at least one pin to rotatably move towards the respective at least one opening to thereby cause the at least one pin to move outwardly through the respective at least one opening.

6. A device as claimed in claim 1 wherein the hollow elongate member has a closed end at a distal end thereof to facilitate insertion of the hollow elongate member into the medullary canal.

7. A device as claimed in claim 6 wherein the distal end of the hollow elongate member is provided with a conical point.

8. A device as claimed in claim 1 wherein the at least one pin carried by said inner member includes a plurality of pins.

9. A device as claimed in claim 1 wherein a proximal end of the inner member is provided with an engaging surface for engaging a torque applying member.

10. A device as claimed in claim 1 wherein the hollow elongate member is provided with a holding surface for holding the hollow elongate member in position and preventing rotation thereof.

11. An intramedullary bone fixation device comprising:
    a hollow elongate member having at least one opening in a side wall thereof, the hollow elongate member being adapted for insertion into a medullary canal of a bone,
    an inner member sized to be slidably receivable within the hollow elongate member, the inner member carrying at least one pin, the inner member having at least one groove in an outer surface thereof, said at least one pin being positioned in the at least one groove when the at least one pin is in a retracted position, at least one said pin being pivotally connected at one end thereof to the inner member, the at least one pin being movable from a retracted position to an extended position in which the at least one pin extends through respective ones of the at least one opening in the hollow elongate member, and wherein the at least one pin is moved to the extended position by placing free ends of the at least one into alignment with the at least one opening and rotating the inner member to thereby extend the at least one pin through the at least one opening, and
    the hollow elongate member and the inner member are of adjustable length.

12. An intramedullary bone fixation device comprising:
    a hollow elongate member having at least one opening in a side wall thereof, the hollow elongate member being adapted for insertion into a medullary canal of a bone, and
    an inner member sized to be slidably receivable within the hollow elongate member, the inner member carrying at least one pin, the at least one pin being movable from a retracted position to an extended position in which the at least one pin extends through respective ones of the at least one opening in the hollow elongate member, wherein at least one said pin has an enlargement at one end thereof and the enlargement rests in a respective hole formed in the inner member and the at least one pin extends along respective grooves formed in an outer surface of the inner member when in the retracted position, said groove extending in a direction that is generally transverse to a longitudinal axis of said inner member, wherein the at least one pin is retained in place by an inner wall of the hollow elongate member and the at least one pin is extended by aligning free ends thereof with the at least one opening in the hollow elongate member and rotating the inner member.

13. A device as claimed in claim 12 wherein a free end of the at least one pin extends slightly beyond the outer surface of the inner member.

14. A device as claimed in claim 13 wherein the free ends of the at least one pin extend into respective ones of the at least one opening when in the retracted position.

15. A device as claimed in claim 13 wherein an inner wall of the hollow elongate member is provided with a groove for receiving the free ends of the at least one pin to thereby allow longitudinal insertion of the inner member into the hollow elongate member.

16. A device as claimed in claim 12 wherein the at least one pin is positioned such that rotation of the inner member causes the enlarged end of the at least one pin to rotatably move towards the respective at least one opening to thereby cause the least one pin to move outwardly through the respective at least one opening.

17. A device as claimed in claim 12 wherein the hollow elongate member has a closed end at a distal end thereof to facilitate insertion of the hollow elongate member into the medullary canal.

18. A device as claimed in claim 17 wherein the distal end of the hollow elongate member is provided with a conical point.

19. A device as claimed in claim 12 wherein the at least one pin carried by said inner member includes a plurality of pins.

20. A device as claimed in claim 12 wherein a proximal end of the inner member is provided with an engaging surface for engaging a torque applying member.

21. A device as claimed in claim 12 wherein the hollow elongate member is provided with a holding surface for holding the hollow elongate member in position and preventing rotation thereof.

22. An intramedullary bone fixation device comprising:
   a hollow elongate member having at least one opening in a side wall thereof, the hollow elongate member being adapted for insertion into a medullary canal of a bone,
   an inner member sized to be slidably receivable within the hollow elongate member, the inner member carrying at least one pin, the at least one pin being movable from a retracted position to an extended position in which the at least one pin extends through respective ones of the at least one opening in the hollow elongate member, wherein at least one said pin has an enlargement at one end thereof and the enlargement rests in a respective hole formed in the inner member and the at least one pin extends along respective grooves formed in an outer surface of the inner member when in the retracted position, wherein the at least one pin is retained in place by an inner wall of the hollow elongate member and the at least one pin is extended by aligning free ends thereof with the at least one opening in the hollow elongate member and rotating the inner member, and
   the hollow elongate member and the inner member are of adjustable length.

23. An apparatus for fixing to a structure, beam, member or the like, comprising:
   a hollow elongate member having at least one opening in a side wall thereof, the hollow elongate member being adapted for insertion into a hole in a structure, beam, member or the like, and
   an inner member that is insertable into the hollow elongate member, the inner member carrying at least one fixing pin, the inner member having at least one groove in an outer surface thereof, said at least one groove extending in a direction that is generally transverse to a longitudinal axis of the inner member, said at least one fixing pin being positioned in the at least one groove when the at least one fixing pin is in a retracted position, the at least one fixing pin being pivotally connected at one end thereof to the inner member, the at least one fixing pin being movable from a retracted position to an extended position in which the at least one fixing pin extends through respective ones of the at least one opening in the hollow elongate member, and wherein the at least one fixing pin is moved to the extended position by placing free ends of the at least one fixing pin into alignment with the at least one opening and rotating the inner member to thereby extend the at least one fixing pin through the at least one opening and into at least one wall defining the hole in a structure, beam, member or the like to fix the apparatus to the structure, beam, member or the like.

24. An apparatus as claimed in claim 23 wherein a free end of the at least one pin extends slightly beyond the outer surface of the inner member.

25. An apparatus as claimed in claim 24 wherein the free ends of the at least one pin extend into respective ones of the at least one opening when in the retracted position.

26. An apparatus as claimed in claim 24 wherein an inner wall of the hollow elongate member is provided with a groove for receiving the free ends of the at least one pin to thereby allow longitudinal insertion of the inner member into the hollow elongate member.

27. An apparatus as claimed in claim 23 wherein the at least one pin is pivotally mounted at one end such that rotation of the inner member causes the pivotally mounted end of the at least one pin to rotatably move towards the respective at least one opening to thereby cause the at least one pin to move outwardly through the respective at least one opening.

28. An apparatus as claimed in claim 23 wherein the at least one pin carried by said inner member includes a plurality of pins.

29. An apparatus for fixing to a structure, beam, member or the like, comprising:
   a hollow elongate member having at least one opening in a side wall thereof, the hollow elongate member being adapted for insertion into a hole in a structure, beam, member or the like,
   an inner member that is insertable into the hollow elongate member, the inner member carrying at least one pin, the inner member having at least one groove in an outer surface thereof, said at least one pin being positioned in the at least one groove when the at least one pin is in a retracted position, the at least one pin being pivotally connected at one end thereof to the inner member, the at least one pin being movable from a retracted position to an extended position in which the at least one pin extends through respective ones of the at least one opening in the hollow elongate member, and wherein the at least one pin is moved to the extended position by placing free ends of the at least one pin into alignment with the at least one opening and rotating the inner member to thereby extend the at least one pin through the at least one opening, and
   the hollow elongate member and the inner member are of adjustable length.

30. An apparatus for fixing to a structure, beam, member or the like, comprising:
   a hollow elongate member having at least one opening in a side wall thereof, the hollow elongate member being adapted for insertion into a hole in a structure, beam, member of the like, and an inner member that is insertable into the hollow elongate member, the inner member carrying at least one fixing pin, the at least one fixing pin being movable from a retracted position to an extended position in which the at least one fixing pin extends through respective ones of the at least one opening in the hollow elongate member, wherein the at least one fixing pin has an enlargement at one end thereof and the enlargement rests in a respective hole formed in the inner member and the at least one fixing pin extends along respective grooves formed in the inner member when in the retracted position, said grooves extending in a direction that is generally transverse to a longitudinal axis of said inner member, wherein the at least one fixing pin is retained in place by an inner wall of the hollow elongate member and the at least one fixing pin is extended by aligning free ends thereof with the at least one opening in the hollow elongate member and rotating the inner member so that the at least one fixing pin extends out of the at least one opening and into at least one wall defining the hole in the structure, beam, member or the like to fix the apparatus to the structure, beam, member or the like.

31. An apparatus as claimed in claim 30 wherein a free end of the at least one pin extends slightly beyond the outer surface of the inner member.

32. An apparatus as claimed in claim 31 wherein the free ends of the at least one pin extend into respective ones of the at least one opening when in the retracted position.

33. An apparatus as claimed in claim 31 wherein an inner wall of the hollow elongate member is provided with a groove for receiving the free ends of the at least one pin to thereby allow longitudinal insertion of the inner member into the hollow elongate member.

34. An apparatus as claimed in claim 30 wherein the at least one pin is positioned such that rotation of the inner member causes the enlarged end of the at least one pin to rotatably move towards the respective at least one opening to thereby cause the least one pin to move outwardly through the respective at least one opening.

35. An apparatus as claimed in claim 30 wherein the at least one pin carried by said inner member includes a plurality of pins.

36. An apparatus for fixing to a structure, beam, member or the like, comprising:

a hollow elongate member having at least one opening in a side wall thereof, the hollow elongate member being adapted for insertion into a hole in a structure, beam, member of the like, an inner member that is insertable into the hollow elongate member, the inner member carrying at least one pin, the at least one pin being movable from a retracted position to an extended position in which the at least one pin extends through respective ones of the at least one opening in the hollow elongate member, wherein the at least one pin has an enlargement at one end thereof and the enlargement rests in a respective hole formed in the inner member and the at least one pin extends along respective grooves formed in the inner member when in the retracted position, wherein the at least one pin is retained in place by an inner wall of the hollow elongate member and the at least one pin is extended by aligning free ends thereof with the at least one opening in the hollow elongate member and rotating the inner member, and the hollow elongate member and the inner member are of adjustable length.

* * * * *